United States Patent
Marzella

(10) Patent No.: US 9,179,924 B2
(45) Date of Patent: Nov. 10, 2015

(54) DRIVING APPARATUSES FOR SURGICAL DEVICES AND SURGICAL DEVICES EQUIPPED WITH SUCH APPARATUSES

(75) Inventor: Michele Giuseppe Renato Marzella, Vasto (IT)

(73) Assignee: Michele Giuseppe Renato Marzella, Vasto, Chieti (IT)

( * ) Notice: Subject to any disclaimer, the term of this patent is extended or adjusted under 35 U.S.C. 154(b) by 98 days.

(21) Appl. No.: 14/006,683

(22) PCT Filed: Mar. 22, 2012

(86) PCT No.: PCT/IB2012/051374
§ 371 (c)(1),
(2), (4) Date: Sep. 23, 2013

(87) PCT Pub. No.: WO2012/127442
PCT Pub. Date: Sep. 27, 2012

(65) Prior Publication Data
US 2014/0012263 A1    Jan. 9, 2014

(30) Foreign Application Priority Data

Mar. 23, 2011  (IT) .............................. PE2011A0003

(51) Int. Cl.
*A61B 17/16* (2006.01)
*A61B 17/00* (2006.01)

(52) U.S. Cl.
CPC ......... *A61B 17/1631* (2013.01); *A61B 17/1624* (2013.01); *A61B 17/1628* (2013.01); *A61B 17/162* (2013.01); *A61B 17/1633* (2013.01); *A61B 2017/0023* (2013.01); *A61B 2017/0046* (2013.01)

(58) Field of Classification Search
CPC . A61B 17/16; A61B 17/1631; A61B 17/1624
USPC ........ 606/79, 80–85, 86 R; 408/8–11, 16, 97, 408/102, 202; 173/2, 4, 11, 176, 181, 217
See application file for complete search history.

(56) References Cited

U.S. PATENT DOCUMENTS

| | | | |
|---|---|---|---|
| 3,120,845 A * | 2/1964 | Horner | 606/180 |
| 2003/0163134 A1* | 8/2003 | Riedel et al. | 606/79 |
| 2006/0111723 A1* | 5/2006 | Chapolini et al. | 606/80 |
| 2006/0217729 A1* | 9/2006 | Eskridge et al. | 606/80 |
| 2008/0215056 A1 | 9/2008 | Miller et al. | |
| 2009/0264940 A1* | 10/2009 | Beale et al. | 606/86 R |

FOREIGN PATENT DOCUMENTS

WO   2004028402 A2   4/2004
WO   2009129026 A1   10/2009

* cited by examiner

*Primary Examiner* — Christopher Beccia
(74) *Attorney, Agent, or Firm* — Robert E. Alderson, Jr.

(57) ABSTRACT

Driving apparatuses for surgical instruments are provided. Such apparatuses are capable of reuse without having to be sterilized in an autoclave. This reduces time as well as costs associated with surgical interventions in the areas of orthopaedic surgery and surgery related to trauma, for example.

8 Claims, 14 Drawing Sheets

DRIVING APPARATUSES FOR SURGICAL DEVICES AND SURGICAL DEVICES EQUIPPED WITH SUCH APPARATUSES

CROSS-REFERENCE TO RELATED APPLICATIONS

This application is a National Phase Application of PCT International Application No. PCT/IB2012/051374, International Filing Date, Mar. 22, 2012, claiming priority to Italian Patent Application No. PE2011A000003, filed Mar. 23, 2011, each of which is hereby incorporated by reference in its entirety.

FIELD OF THE INVENTION

The present invention relates to a driving apparatus for a surgical device of the type driven by a motor, destined in particular for the manipulation of skeletal bones, such as for trapanation, drilling or resection, in the specific field of orthopaedics and traumatology, but also in the wider field of general surgery.

The invention also relates to a surgical device equipped with such driving apparatus.

BACKGROUND OF THE INVENTION

The orthopaedic appliances used for the surgical manipulation of bones are of the type driven pneumatically, with compressed air or an electric motor. Electrically driven devices are powered both from the mains power supply and by battery.

In addition, surgical devices are generally multi-function in the sense that they can drive various surgical instruments, even though the type dedicated to performance of a single function exist, such as in the case of sawing bones, which entails driving characterised by a rectilinear, alternate movement, therefore not circular.

The intended use of such surgical appliances presumes compliance with extremely strict safety standards. In this context, it is easy to see that the functioning of the driving apparatus of surgical devices—also called "drivers" in the present invention—must not present any interruption during the surgical operation. This means that drivers with a relatively long lifespan must be provided: this is the reason for which such drivers are subject to stringent testing to reduce as far as possible—it not being possible to eliminate them completely—interruptions to functioning during surgery.

In addition, when batteries are used to power electric motor drivers, they must have an appropriate voltage and long life: classically, the lithium type is preferred.

In certain cases the driver of the surgical device must also guarantee the possibility of varying the speed of the instrument, depending on the requirements related to the type of operation.

Overall, these drivers must be as light, manageable and easy to use as possible: from this point of view, one may easily see that the ergonomic nature of the grip of the driver is practically obligatory.

Of course, the question of asepsis also concerns the surgical appliances fitted with instruments intended for general surgery.

Normally, two main solutions are essentially used to ensure asepsis. A first solution consists of making a driver, preferably of the electric motor type, bearing a fully waterproof casing, inside which the electric motor, the power supply battery of such motor and the electric connection cables are enclosed.

After each operation, such driver with waterproof casing is subjected, of course jointly with the surgical instrument (or surgical instruments in the case in which various have been used during the operation), to sterilisation in an autoclave, so as to make it suitable for another operation. Such solution has the advantage of permitting repeated use in sterile conditions of the waterproof driver. However, this is very expensive since making the driver waterproof and sterilising it requires, on the one hand, the use of appropriate materials and, on the other, the use of a specific manufacturing procedure, factors which inevitably reflect on the final costs, necessarily high, of such type of driver.

In addition, the lifetime of the device is considerably reduced as a result of the thermal stress imposed on the driver and the components enclosed within the casing and despite the measures adopted for its realisation (these measures regard the quality and appropriate thickness of the plastic material which the casing is preferably made from). In any case, the reduced lifespan of a waterproof driver—and therefore the need to replace it frequently—contributes, together with the waterproofing of its casing and the sterilisation in an autoclave, to making the relative cost of such solution even higher.

A second solution is of the disposable, single-use type and entails using a driver destined for use only once, thereby eliminating the need to subject it to sterilisation in an autoclave. This enables the use of less expensive materials and components even though the once-only use of such driver ends up heavily influencing costs, in that a different driver must be used for every operation.

From the above, the fact that both the extreme solutions used in the prior art, that is to say of a reusable waterproof driver and of a disposable driver, share the disadvantage of high maintenance and/or running costs, clearly emerges.

SUMMARY OF THE INVENTION

The present invention aims therefore to make driver apparatuses for surgical instruments which better satisfy the needs of the art compared to the devices of the same type used in the prior art and which proposes devices (or drivers) for surgical instruments as described and claimed herein.

The invention also relates to a surgical appliance of the type driven by an electric motor, and therefore necessarily associated with a driver for the manipulation of skeletal bones, especially in the field of orthopaedics and traumatology, which is fitted with a driver apparatus according to the present invention as described and claimed herein.

One advantage of the motor driver according to the present invention is that the aseptic nature of its use is ensured without having to subject it to the process of sterilisation in an autoclave, onerous both in terms of thermal stress and costs.

Another advantage is the possibility of rapidly replacing the drive motor or power supply battery even during an operation, without by so doing foregoing the required aseptic conditions.

A further advantage, certainly not to be overlooked, and direct consequence of the two advantages previously indicated, is the considerable reduction in production, maintenance and running costs.

Of course, other advantages emerge from the present invention as described and claimed herein.

Non-limiting embodiments of a motor driver for surgical instruments according to the invention is described below by way of non-limiting examples with reference to the appended drawings.

DETAILED DESCRIPTION

Figure 1:
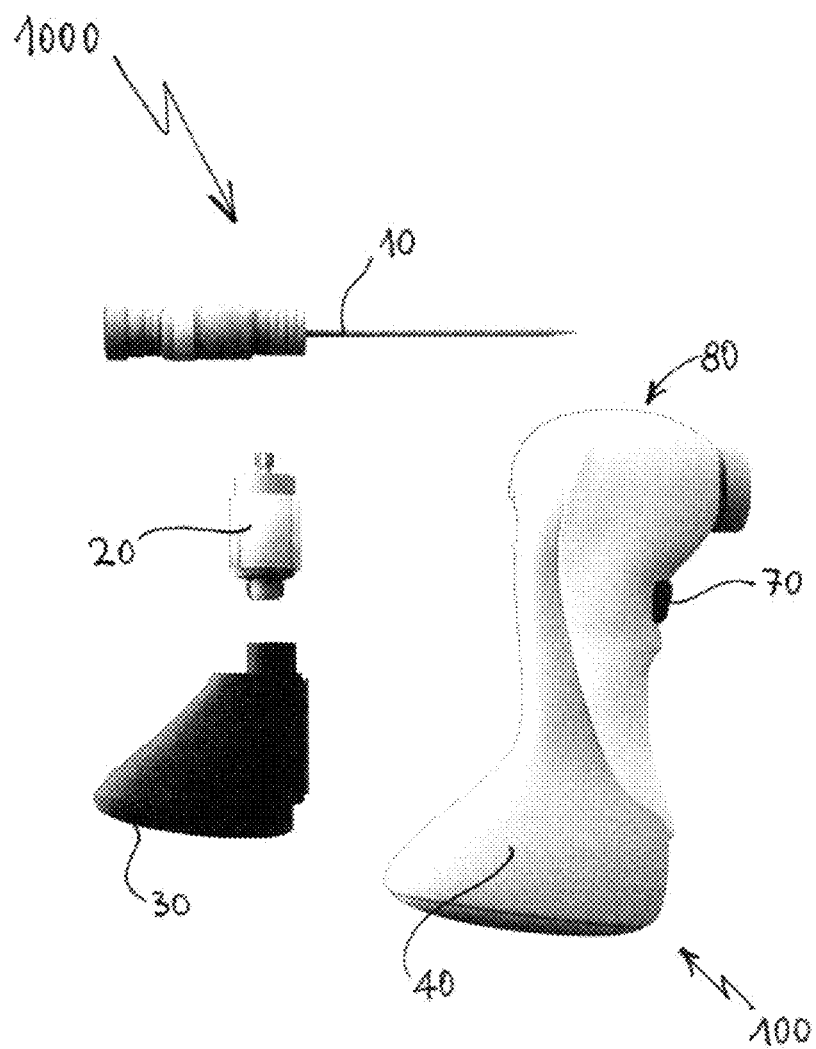
FIG. 1 is an exploded view in vertical elevation of the essential constituent elements of the driver according to the invention, also showing a surgical instrument destined to be driven by such driver.
Figure 2:
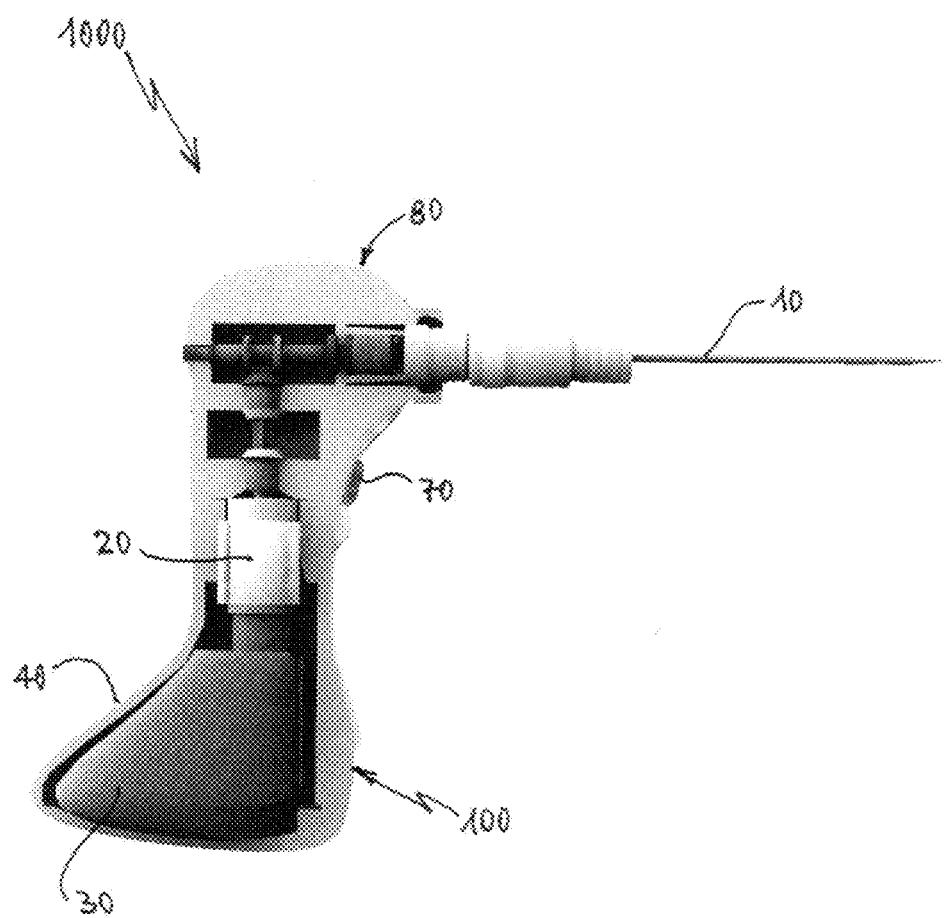
FIG. 2 corresponds to FIG. 1 and differs from it in that the elements shown in the latter are represented separately, while in the present drawing they are shown positioned inside a casing of the driver, also showing the application of a surgical instrument to the proximal end of the driver.

The driver 100 which the following description relates to is of the type destined to drive a surgical instrument 10 by means of an electric motor 20 in turn powered by a battery 30: the conformation of such battery meets the need to adapt to the ergonomic configuration, in particular of the grip 40 (see in particular FIG. 2) of the apparatus 100. The surgical instrument 10 is connected to the apparatus 100 by a shaft 60, corresponding to the driven shaft, in turn driven by a shaft 50, corresponding to the drive shaft: of course, the driven shaft is kept in position in an appropriate manner, clearly shown in the drawings. A control button 70, to turn the driver 100 on and off, is built in to the front wall of the latter. All the previous elements—the electric motor 20, the drive shaft 50, the driven shaft 60 and the power supply battery 30—are destined to be housed in a casing 80 (see FIG. 2), of which the ergonomic grip 40 is an integral part. According to the invention, the driver apparatus 100 also comprises an interconnection device 90 of the drive shaft 50 and the driven shaft 60, of which a proximal end 91 and distal end 92 may be distinguished. Such interconnection device 90 acts in conjunction with an isolation—or separation—means 200 between the drive shaft 50 and the driven shaft 60 and encloses, at least partially, the interconnection device 90 between these two shafts 50 and 60.

Such isolation device is intended to avoid any direct contact between the drive shaft 50 and the driven shaft 60 so as to prevent the propagation of any accidental contamination from the drive shaft 50 to the driven shaft 60 and thus to the surgical instrument 10.

Within the scope of this invention, the casing 80 is removable and interchangeable and is destined to be sterilised before the insertion of the motor 20, the battery 30 and the control button 70 as well as the necessary electric connection cables (not shown in the drawings for the sake of simplicity) inside it, and therefore before use.

Figure 4:
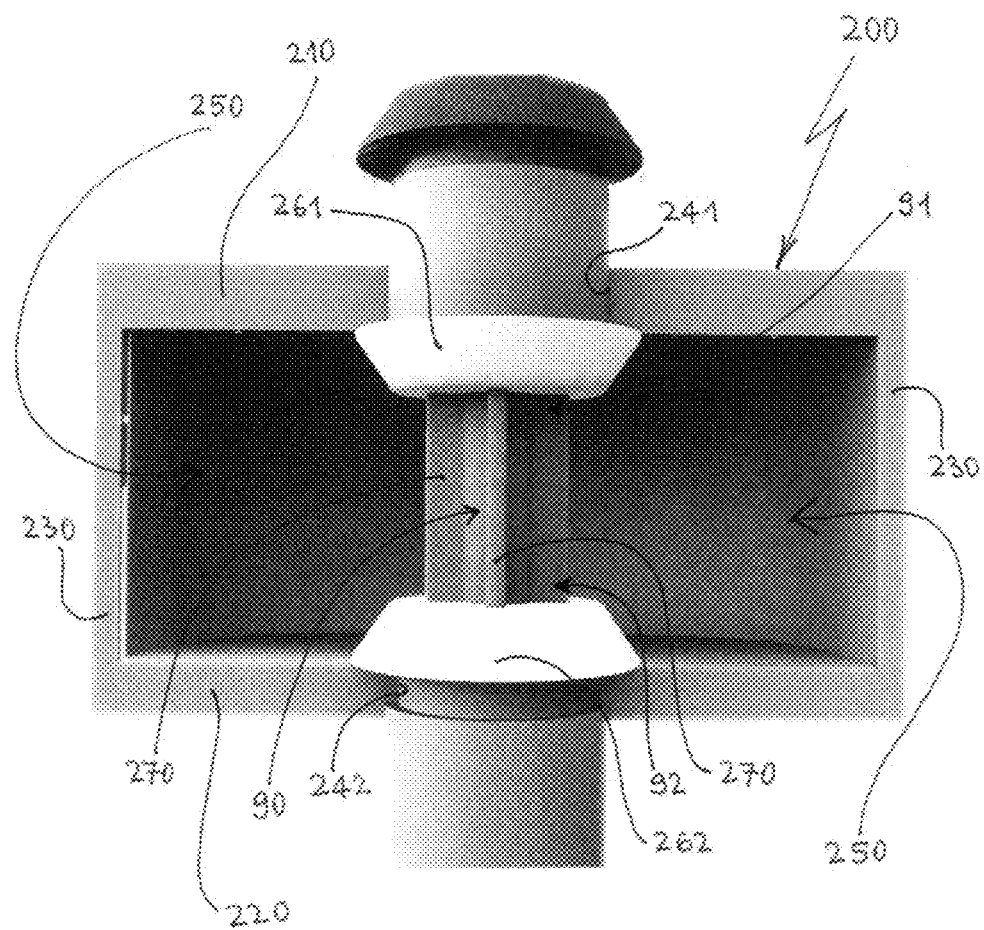
FIG. 4 is a further detail, on an even larger scale than FIG. 4, of FIG. 2 highlighting the interconnection device between the drive shaft and the driven shaft and showing in particular the isolation or separation means of these two shafts, according to the present invention.
Figure 5:
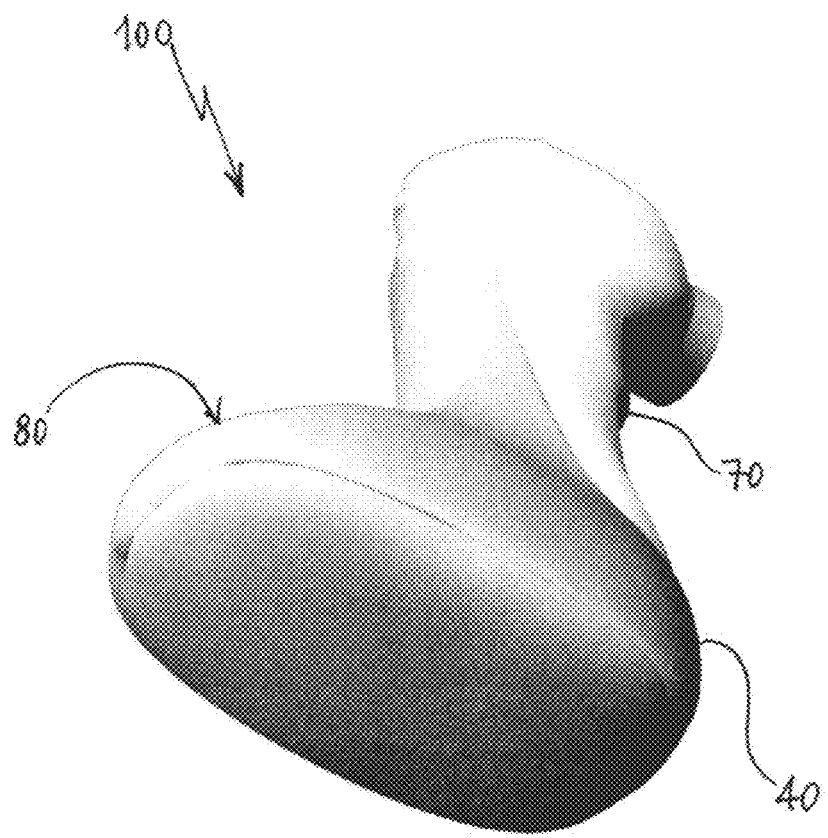
FIGS. 5, 6 and 7 are three perspective views respectively of the driver according to the invention in its entirety, of the driver at the moment it is about to receive inside it the electric motor and of the driver at the moment it is about to receive inside it, according to a logical sequence, the power supply battery of such motor; these figures also show the ergonomic nature of the apparatus in its entirety.
Figure 6:
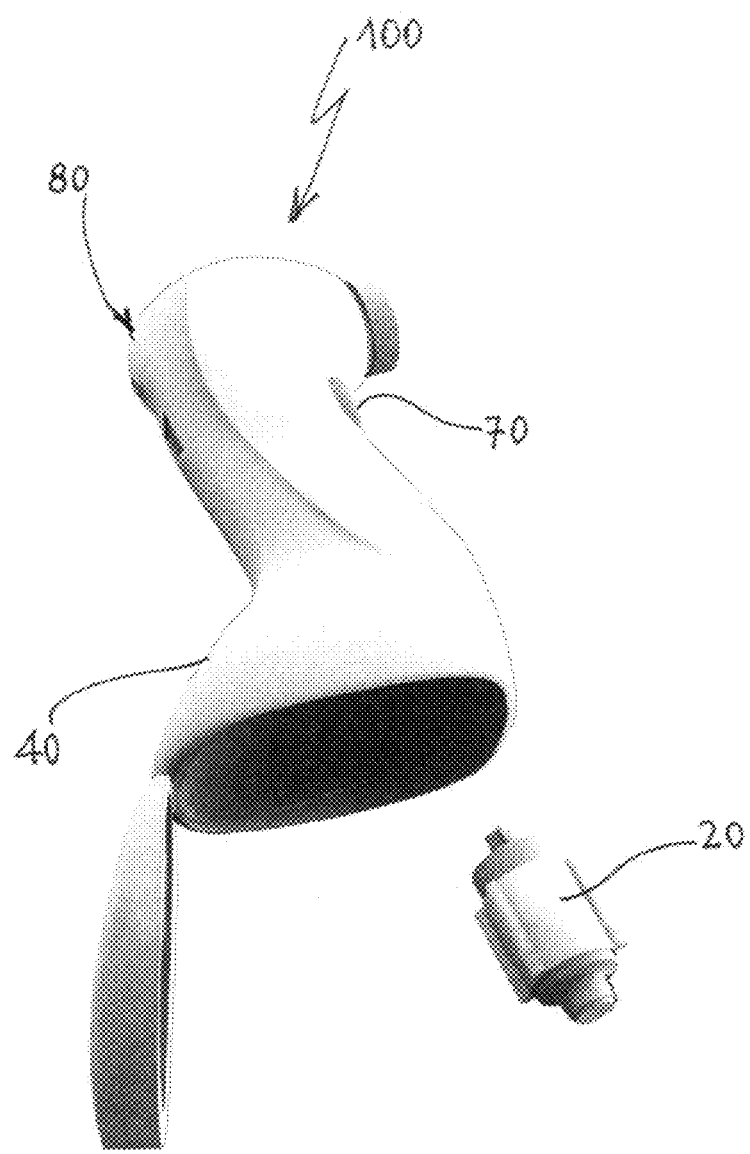
Figure 7:
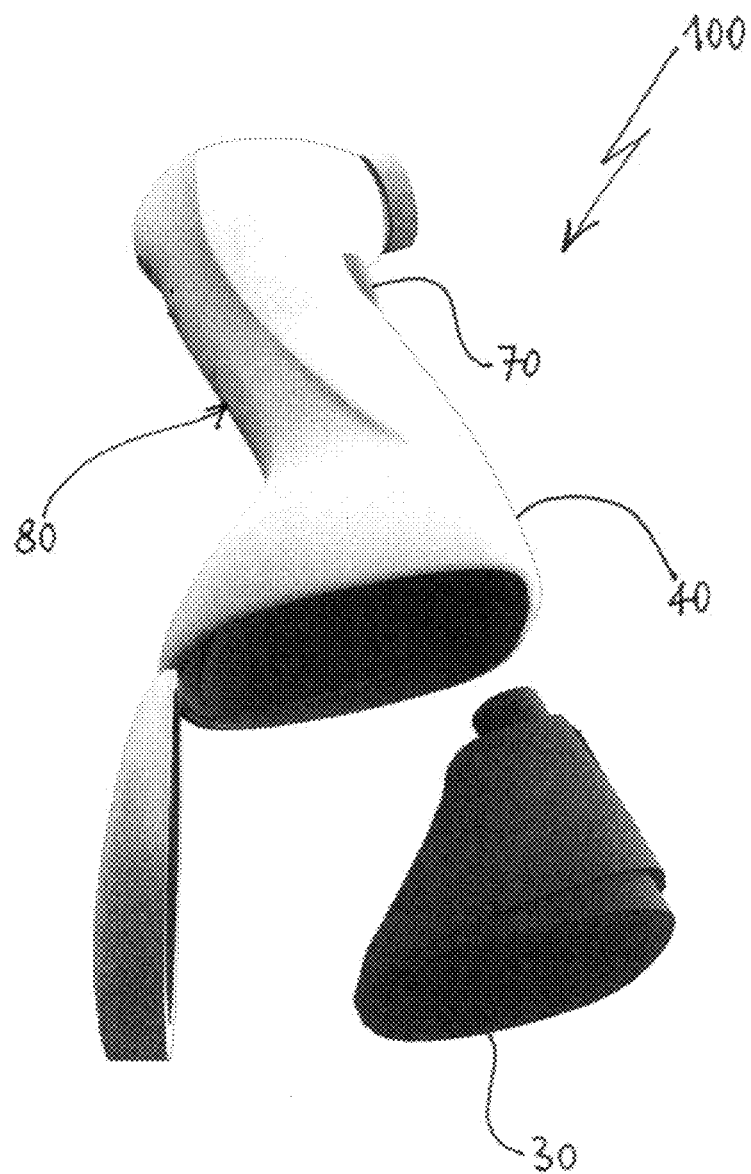
Figure 8:
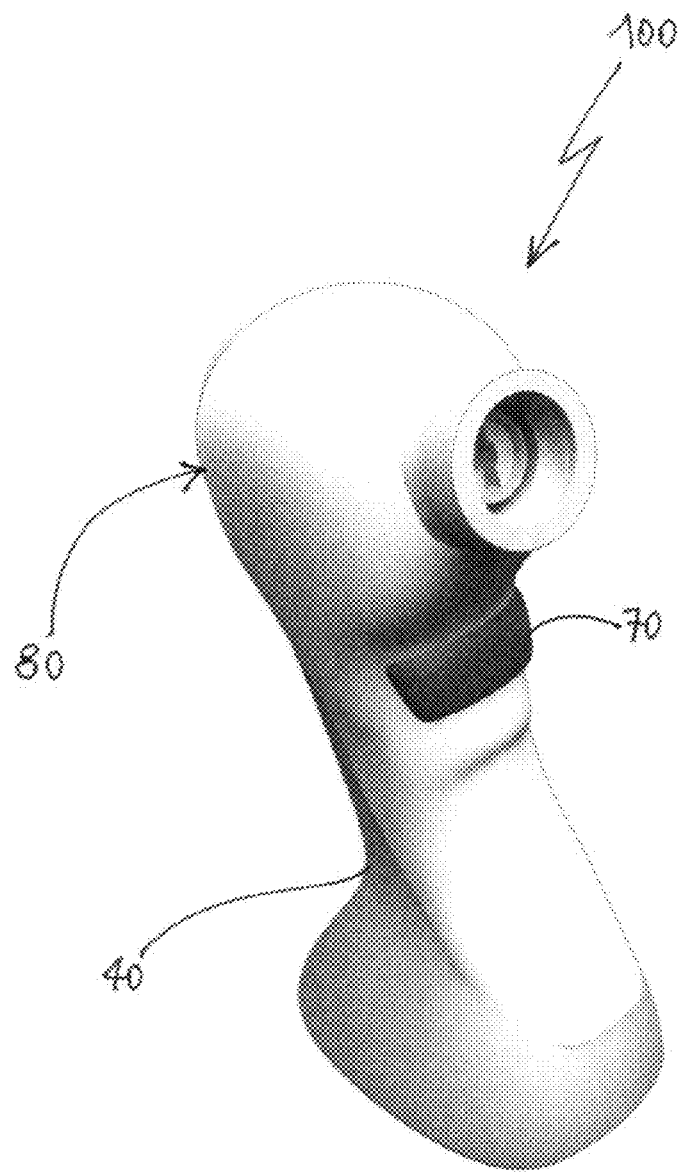
FIGS. 8, 9, 10, 11, 12 and 13 show the same number of perspective views of the apparatus according to the invention, destined to highlight the greater number of construction details of the same: respectively being, in the order indicated, a view from a left and right anterior angular observation point, anterior front view, a posterior front view and of a right and left lateral view.
Figure 9:
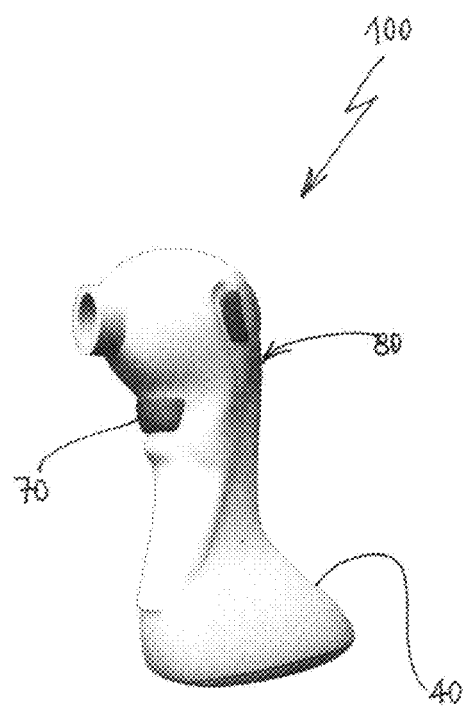
Figure 10:
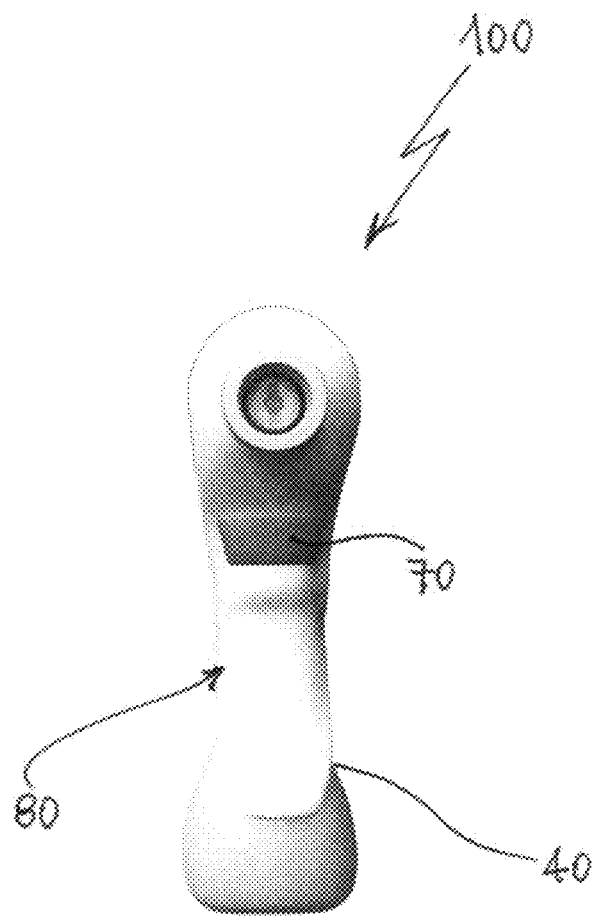
Figure 11:
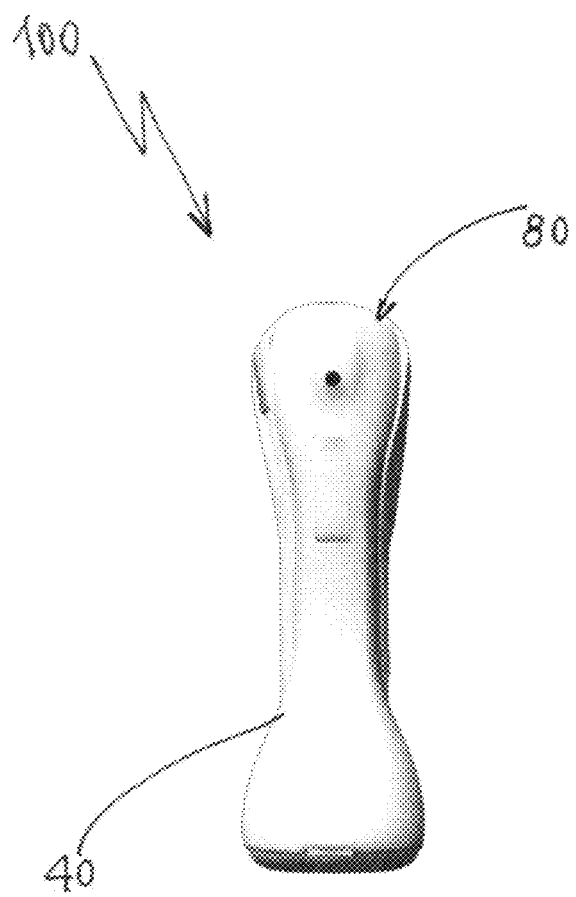
Figure 12:
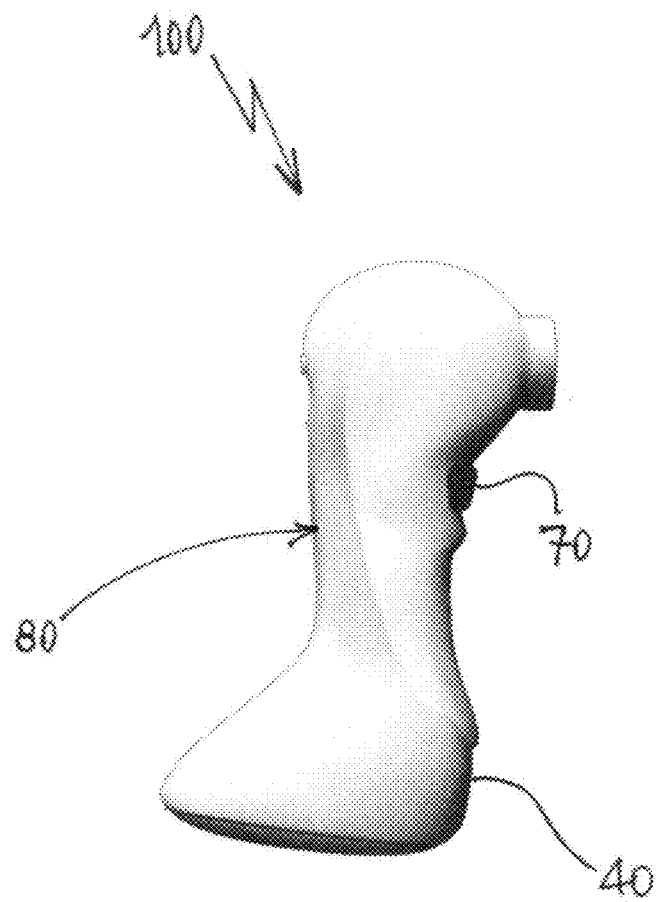
Figure 13:
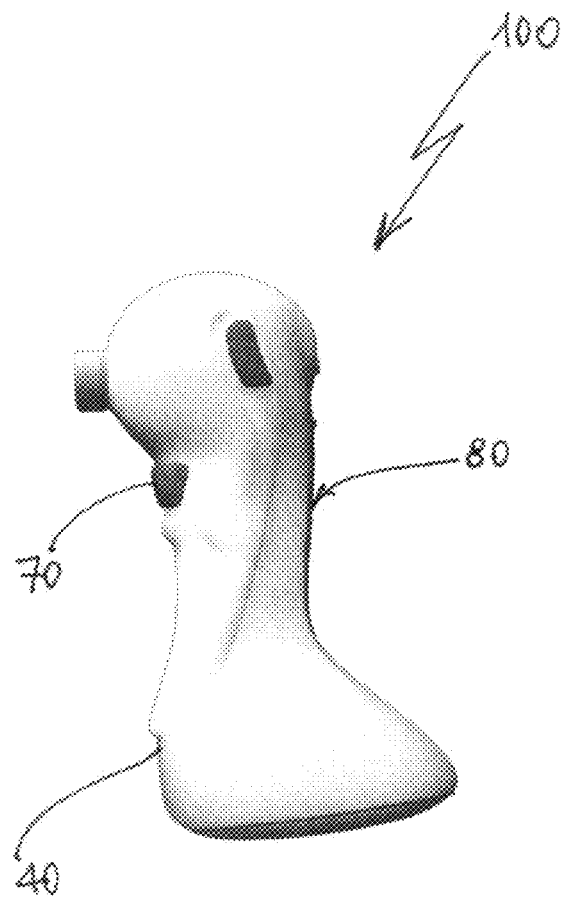
Figure 14:
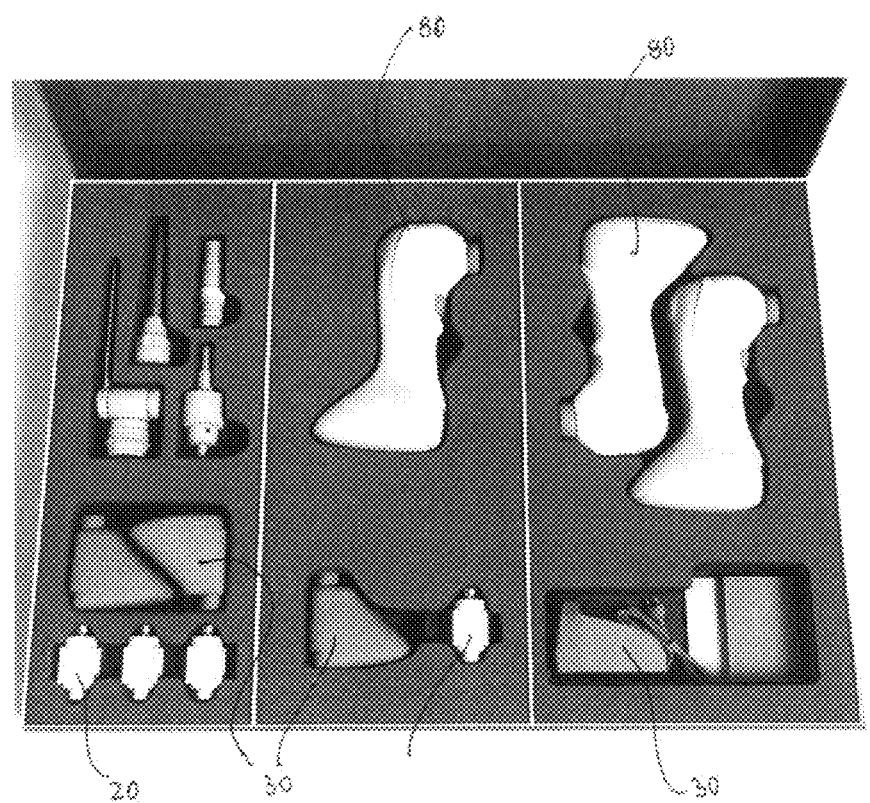
FIG. 14 is a view from above of a possible kit, placed in a containment case, destined for the commercialisation of the apparatus according to the invention.

According to a preferred but not exclusive embodiment of the driver according to the invention, the separation (or isolation) means consists of a chamber 200 impermeable to pathogens (see in particular FIG. 4), Such chamber 200 defines an inner space 250, through co-operation of a proximal transversal wall 210, a distal transversal wall 220 and an axial wall 230 (the transversal or axial nature of such walls refers to the axis of the drive shaft 50, as shown in the drawings).

The impermeabilisation chamber 200 is destined to be positioned, at least partially, around the interconnection device 90 and comprises, so as to assure the necessary impermeabilisation, a proximal ring 261 and distal ring 262, ensuring the seal, respectively of a proximal axial opening 241 and a distal axial opening 242 made respectively in the proximal transversal wall 210 and in the distal transversal wall 220 of the impermeabilisation chamber 200.

The sealing rings 261, 262 are suitable for being kept in position through axial compression ribs 270 integral with the interconnection means 90.

The interconnection device 90 advantageously has its proximal end 91 and its distal end 92 shaped in such a way as to ensure the rapid and stable positioning of such device inside the casing 80 by means for example of a simple recessing or slotting together of its ends (not shown in the drawings for reasons of clarity but known to the person skilled in the art).

Figure 3:
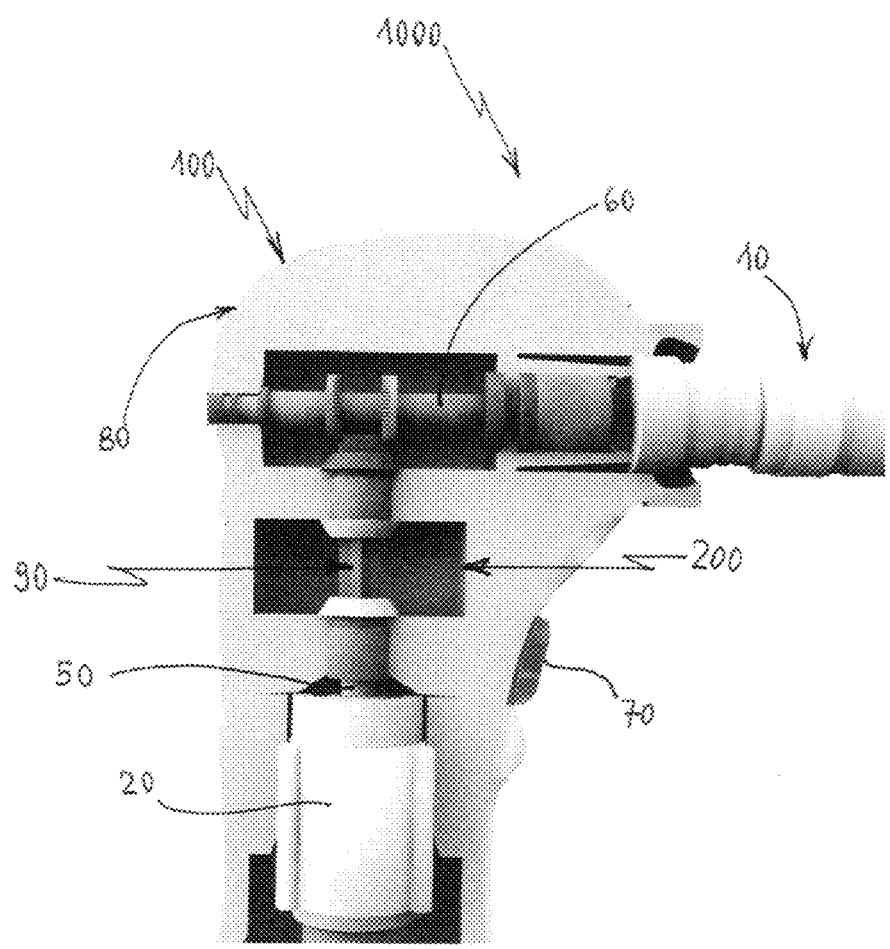
FIG. 3 shows a detail, on a larger scale, of FIG. 2, highlighting the interconnection device between the drive shaft and the driven shaft.

According to the invention, the impermeabilisation chamber 200 is made preferably in the inner wall of such casing 80, as shown in particular in FIG. 3: in such case the casing and the chamber are therefore made in one piece.

An alternative solution to such last arrangement consists of making the casing 80 and the chamber 200 in separate pieces: in such case, the chamber is designed to be inserted around the interconnection device 90 and to be positioned inside the casing in a suitable seat made in the inner wall of such. Such alternative solution has not been illustrated so as not to burden the description and the already extensive number of drawings attached thereto, but its practical realisation falls within the knowledge of a person skilled in the art on the basis of the description—albeit concise, but complete of the essential elements—which has just been given.

Preferably but not necessarily exclusively, the impermeabilisation chamber 200 is cylindrical.

In addition, it may be advantageous to position a further sealing ring (not shown in the drawings for simplicity's sake) in the grip 40 of the appliance 200, at the interface with the control means 70 built in to such grip.

Both the sealing rings 261, 262, respectively proximal and distal, of the impermeabilisation chamber 200 and the sealing ring of the control means 70, are advantageously removable.

The present invention also relates to a surgical appliance 1000—of the type driven by an electric motor, and therefore necessarily associated with a driver—for the manipulation of skeletal bones, especially in the field of orthopaedics and traumatology, which is fitted with a driver apparatus 100 according to the present invention.

The invention claimed is:

1. A driving apparatus for a surgical instrument suitable for being connected to the driving apparatus by a driven shaft, in turn suitable for being driven by a drive shaft, comprising:
   driver elements for driving the surgical instrument by the drive shaft;
   power supply elements for the driver elements;
   control elements for the driver elements;
   a casing suitable for containing the driver elements, the power supply elements and the control elements and which comprises an ergonomic grip for manipulating the appliance, the control elements being integrated in a wall of the casing,
   an interconnection device of the drive shaft and the driven shaft, with a proximal end and a distal end;
   isolation elements between the drive shaft and driven shaft and, at least partially, of the interconnection device between these two shafts, which prevent any direct contact between the drive shaft and the driven shaft, so as to prevent the propagation of accidental contamination from the drive shaft to the driven shaft and to the surgical instrument;
   wherein the casing is suitable for being sterilised before inserting in it the driver elements, the power supply elements and the control elements, and
   wherein such casing is removable and interchangeable, and wherein:
   the isolation elements comprise a chamber impermeable to pathogens, said chamber defining an inner space, through cooperation of a proximal transversal wall, a distal transversal wall and an axial wall, which is arranged at least partially around the interconnection device and which comprises a proximal ring and a distal ring ensuring sealing, respectively, of a proximal axial opening and a distal axial opening arranged, respectively, in the proximal transversal wall and in the distal transversal wall of the chamber.

2. The apparatus of claim 1, wherein the sealing rings are configured to be maintained in position through axial compression ribs which are integral to the interconnection elements, and wherein
   the interconnection device has its proximal end and its distal end shaped in such a way as to ensure the rapid and stable positioning of such device inside the casing.

3. The apparatus of claim 1, wherein the chamber is made in an inner wall of the casing, so that the casing and the chamber are in one piece.

4. The apparatus of claim 1, wherein the casing and the chamber are made in separate pieces, the chamber being configured to be positioned at least partially around the interconnection device and to be kept in position inside the casing in a seat made in an inner wall of the casing.

5. The apparatus of claim 1, wherein the chamber is cylindrical.

6. The apparatus of claim 1, wherein a sealing ring is configured to be positioned in the grip of the device, at the interface with the control elements integral with such grip.

7. The apparatus of claim 1, wherein both the sealing rings of the chamber and the sealing ring of the control elements are removable.

8. A surgical apparatus for manipulation of skeletal bones, comprising a surgical instrument, of a motor-driven type, and a driving apparatus according to claim 1.

* * * * *